United States Patent [19]
Gabelich et al.

[11] Patent Number: 5,632,881
[45] Date of Patent: May 27, 1997

[54] MEASURING MAGNESIUM CONCENTRATIONS IN MOLTEN METAL ALLOYS

[75] Inventors: Stephen A. Gabelich, Long Beach; John McHardy, Westlake Village, both of Calif.

[73] Assignee: Hughes Aircraft Company, Los Angeles, Calif.

[21] Appl. No.: 491,139

[22] Filed: Jun. 16, 1995

Related U.S. Application Data

[63] Continuation of Ser. No. 225,629, Apr. 11, 1994, abandoned.

[51] Int. Cl.$^6$ ................................................. G01N 27/416
[52] U.S. Cl. .................. 205/781.5; 204/400; 204/413; 205/775; 205/790
[58] Field of Search ............................ 204/400, 413, 204/422, 423, 433; 205/775, 781.5, 790

[56] References Cited

U.S. PATENT DOCUMENTS

| | | | |
|---|---|---|---|
| 3,575,834 | 4/1971 | Hoole et al. | 204/435 |
| 4,601,810 | 7/1986 | Tiwari et al. | 204/413 |
| 4,882,032 | 11/1989 | Tiwari | 204/422 |
| 5,262,038 | 11/1993 | Indig et al. | 204/435 |

OTHER PUBLICATIONS

A.A. Dubreuil et al, in Light Metals, L.G. Boxall, Ed., The Metallurgical Society, Inc., pp. 495–499 (1988) Month Unavailable.
D.H. DeYoung, Abstract #763, Fall Meeting of the Electrochemical Society (1990) Month Unavailable.
W.C. Mangalick, in Light Metals, The Metallurgical Society of AIME, pp. 613–634 (1974) Month Unavailable.
B.L. Tiwari, Journal of Metals, 34(9) pp. 54–58 (1982) Month Unavailable.
M.E. Smith, Conservation and Recycling, 6(1–2), pp. 33–40 (1983) Month Unavailable.
B.L. Tiwari, Metallurgical Transactions A, 18 (A), pp. 1645–1651 (1987) Month Unavailable.
G.R. Belton et al, Transactions of the Metallurgic Society of AIME, 245 (10), pp. 2189–2193 (1959) Month Unavailable.
E.E. Lukashenko et al, Russian Metallurgy (Metally), 5, pp. 69–72 (1971) Month Unavailable.
M.M. Tsyplakova et al, Journal of Applied Chemistry of the USSR, 42 (71), pp. 2498–2503 (1989) Month Unavailable.
Agrawal et al, "a Silver–Silver Chloride Reference Electrode for the High Temperature and High Pressure Electrochemistry", *Corrosion*, Jun. 1977.

*Primary Examiner*—T. Tung
*Attorney, Agent, or Firm*—M. E. Lachman; M. W. Sales; W. K. Denson-Low

[57] ABSTRACT

A simple robust sensor probe for determining the magnesium concentration in molten metal alloys in real-time. The probe provides needed process control information in molten metal technologies and has particular application to processes for removing magnesium impurities from scrap aluminum. The probe employs a specially constructed electrochemical concentration cell adapted for repeated immersions into vessels containing molten metal alloys. Specifically, the probe comprises two electrodes, both inert to a molten salt layer, to the molten metal (aluminum), and to magnesium. One electrode comprises an inverted molybdenum cup, a magnesium reference material, and a fibrous ceramic wick, e.g., yttrium oxide, for retaining molten salt therein in contact with the magnesium reference material when the sensor probe is first inserted into the molten salt layer and then into the molten aluminum layer. A readout between the two electrodes provides a measure of the electromotive force and thus a measure of the concentration of magnesium in molten aluminum during demagging of the molten aluminum.

15 Claims, 5 Drawing Sheets

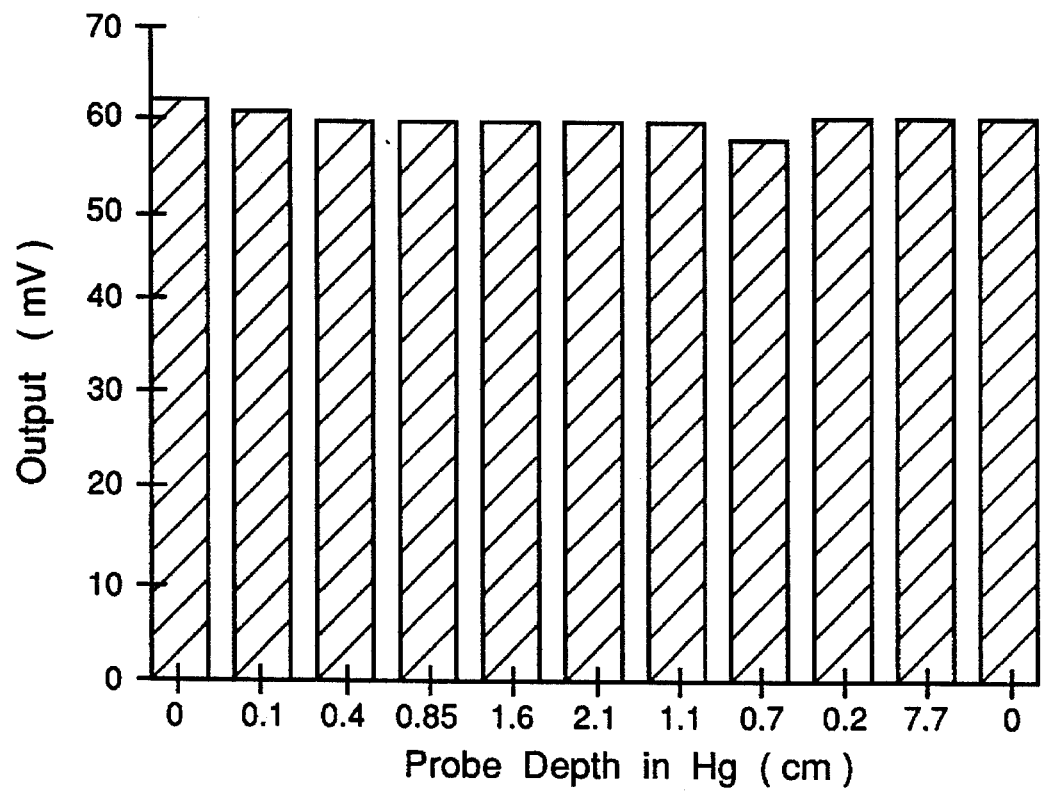
FIG. 7.
FIG. 8.
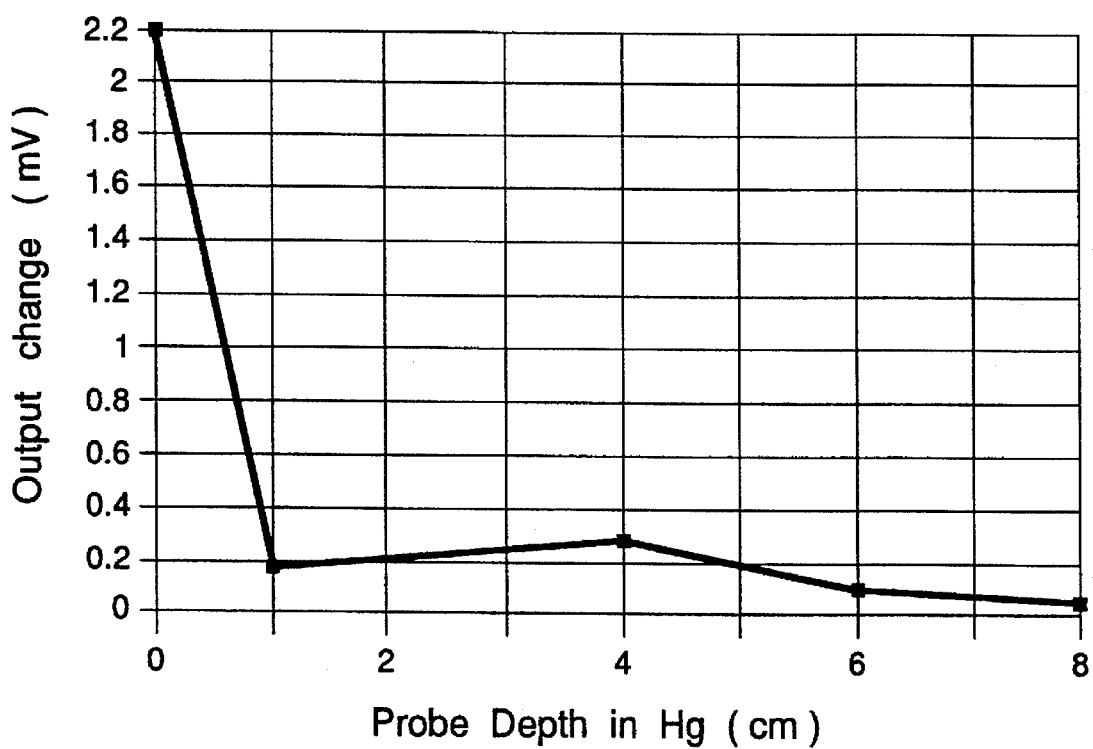

MEASURING MAGNESIUM CONCENTRATIONS IN MOLTEN METAL ALLOYS

This is a continuation application Ser. No. 08/225,692 filed Apr. 11, 1994, now abandoned.

BACKGROUND OF THE INVENTION

1. Field of the Invention

The present invention relates generally to measuring magnesium concentrations in molten metal alloys, and, more particularly, to measuring the concentration of magnesium in molten aluminum alloys.

2. Description of Related Art

Great interest exists within the aluminum industry in the possibility of real-time monitors for molten metal processing. Specifically, work is in progress to develop an electrolytic "demag" process for removing magnesium impurities from scrap aluminum. The demag process is designed to reduce the magnesium content in the scrap aluminum to less than 0.1%. A real-time magnesium sensor is needed to determine when this process is complete, since continuing electrolysis to a magnesium concentration much below 0.1% would waste both time and electric power.

A magnesium sensor has been described by B. L. Tiwari, "Electrochemical Probe for Measuring Magnesium Concentration in Molten Aluminum", U.S. Pat. No. 4,601,810, issued Jul. 22, 1986. The sensor of this reference, is based on the electrochemical concentration cell:

[Mg(l)]||[MgCl$_2$ CaCl$_2$(l)]||[Mg in Al(l)], where "l" denotes liquid (molten material).

The electrode gives a reliable indication of the magnesium content of molten aluminum and is not appreciably affected by the presence of other alloying elements. The measured electrode potential E varies with magnesium content and temperature exactly as predicted by the Nernst Equation:

$$E = -\frac{RT}{2F} \ln[Mg]$$

where R is the gas constant, T is the absolute temperature, F is the Faraday constant, and [Mg] is the thermodynamic activity of magnesium in the aluminum. However, the sensor was optimized for single use laboratory measurements and is unsuitable for multiple-use, industrial applications. Among the drawbacks are high materials and construction costs, a short operating life, and the loss of contained liquids (electrolyte and magnesium) when the probe is withdrawn from the melt.

A Canadian group developed lithium and sodium ion sensors using (solid) β" alumina as the electrolyte; see, A. A. Dubreuil et al, "Solid Electrolyte Probes to Monitor the Alkali and Alkaline Earth Content of Molten Aluminum" in Light Metals, L. G. Boxall, Ed., The Metallurgical Society, Inc., pp. 495-499 (1988). However, the investigators have not been able to extend the approach to magnesium.

Alcoa developed a successful lithium electrode using (solid) fused silica as the electrolyte; see, D. H. DeYoung, "Lithium Sensor for Molten Aluminum-Lithium Alloys", Abstract #763, Fall Meeting of the Electrochemical Society (1990). However, no results for other metals have been published.

Despite extensive research, no practical sensor has yet been commercialized for monitoring magnesium in molten aluminum. Thus, there remains a need for a practical sensor for monitoring the presence of magnesium in molten aluminum.

SUMMARY OF THE INVENTION

In accordance with the present invention, a sensor probe is provided for measuring the concentration of magnesium in molten aluminum during demagging. The sensor probe comprises a fibrous yttrium oxide wick, a magnesium reference material, a protective inverted molybdenum cup for containing the magnesium and providing electrical contact thereto, molybdenum leads shrouded in an inert gas, a voltage readout, and a graphite contact to complete the electrical circuit.

Whereas prior art devices were suitable only for one-time use and the complexity of their design limited their use to laboratory systems, the simple, robust design of the present invention enables the collection of process control information. Such information is required in order to maximize operating efficiency of magnesium removal from molten aluminum.

BRIEF DESCRIPTION OF THE DRAWINGS

FIG. 7, on coordinates of sensor output (in millivolts) and probe depth in mercury (in centimeters), is a bar chart of displaying the output of the probe at different depths in mercury; and FIG. 8, on coordinates of sensor output change (in millivolts) and probe depth in mercury (in millimeters), is a plot of indium concentration in mercury as a function of depth in mercury.

DESCRIPTION OF THE PREFERRED EMBODIMENTS

Figure 1:
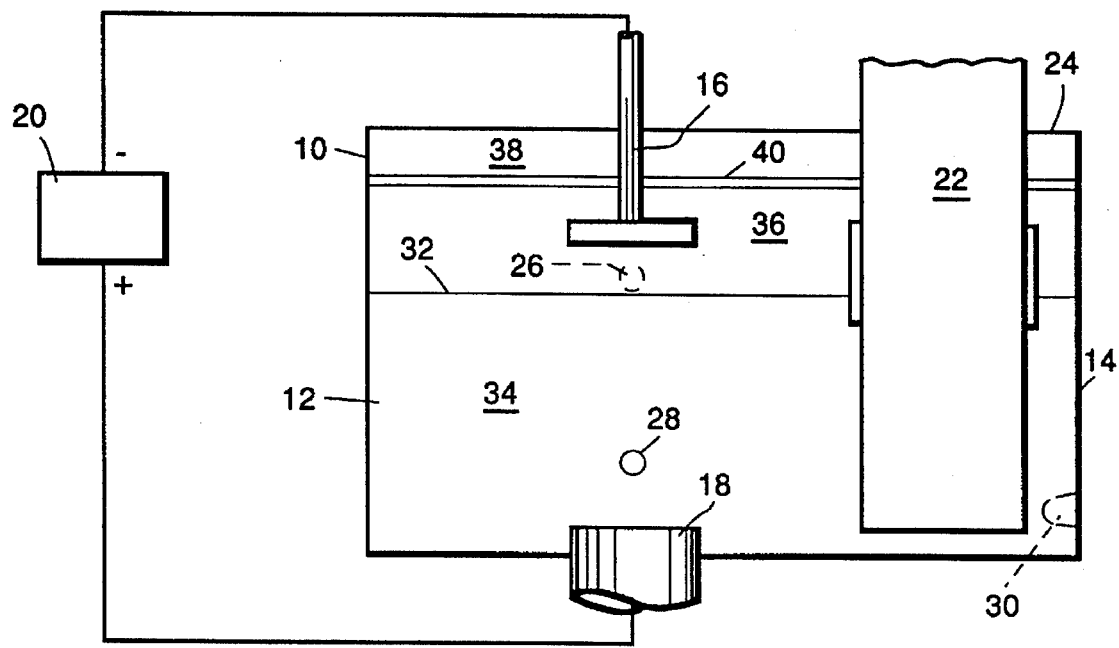
FIG. 1 is a schematic view of apparatus utilized to electrochemically purify scrap aluminum by extracting magnesium from the scrap.

Referring now to the Figures, wherein like numerals designate like elements throughout, FIG. 1 depicts an example of apparatus used for demagging scrap aluminum. As shown in FIG. 1, a fully sealed furnace or reaction vessel 10 provides a closed environment for the removal of magnesium from scrap aluminum and for enabling purified aluminum to be drawn from the closed reaction vessel. The working volume of the reaction vessel 10 is divided into a refining zone 12 and a heating/pouring zone 14. Positioned in the refining zone 12 is a cathode 16 positioned above an anode 18. The cathode and anode are connected to a source of direct current 20. Preferably, cathode 16 is formed of mild steel, while anode 18 is formed of graphite. A heater 22 is positioned in heating/pouring zone 14. A cover 24 in the otherwise closed top of the reaction vessel 10 is opened so that scrap aluminum in molten form may be placed into the vessel. Various openings 26, 28, and 30 are provided in the reaction vessel 10 and are closable by suitable means. Opening 26 is used as an electrolyte/separated magnesium drain, while openings 28 and 30 are used as egresses for removal of refined aluminum from the reaction vessel 10.

In the operation of the demagging process, scrap aluminum containing magnesium impurities in molten form is placed into heating/pouring zone 14 through the opening uncovered by cover 24, and thus within refining zone 12 to approximately meet the lowermost portion of opening 26, indicated generally by a level indicated by line 32. Reference numeral 34 generally designates molten matter comprising either the molten scrap aluminum prior to purification or the purified aluminum obtained therefrom.

An electrolyte 36 of calcium chloride, magnesium chloride, potassium chloride, and sodium chloride is placed above the molten scrap aluminum to a depth sufficient to at least partially cover the cathode 16. Magnesium chloride is required for operation of the electrochemical cell. The other chlorides are added so as to provide a mixture of chlorides having a density intermediate between that of magnesium and aluminum.

A space 38 is provided for an inert gas, for example, argon. Upon application of electrical energy, the magnesium is ionized and collected at the cathode 16, thereby forming a layer 40 of molten magnesium. After a suitable period of time, when the molten scrap aluminum is sufficiently purified of the magnesium impurities, one or both tap holes 26 and 28 are opened in order to draw off the purified aluminum.

Figure 2:
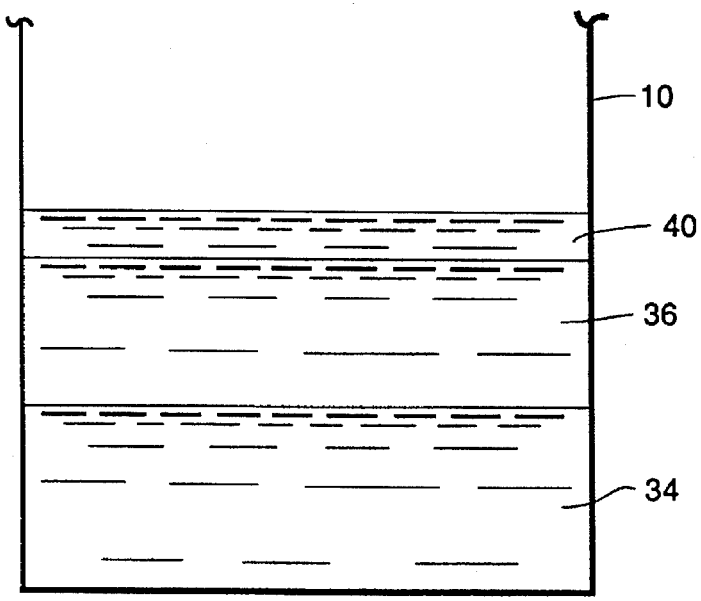
FIG. 2 is a cross-sectional view of a demag reaction vessel (demag cell) used in the apparatus of FIG. 1.

FIG. 2 illustrates details of the demag reaction vessel 10, or demag cell, for removing magnesium from aluminum. The cell 10 is charged with molten aluminum containing magnesium impurities, designated as layer 34; magnesium is removed during the demag purification process. A molten chloride salt layer 36 is provided over the molten aluminum. During the purification process, a molten magnesium layer 40 forms on top of the molten salt layer 36.

In accordance with the present invention, a sensor probe 42 is provided to measure the magnesium concentration of the molten aluminum during the demag processing to thereby provide a real-time measurement. Use of the sensor probe 42 of the present invention permits termination of the demag process when the desired maximum level of magnesium impurities is achieved, such as 0.1 weight percent. By monitoring the magnesium concentration in molten aluminum in real time, the demagging process can be terminated at the desired level of magnesium impurity without using undue additional energy and time that would further reduce the magnesium concentration to a lower level than required.

Figure 3:
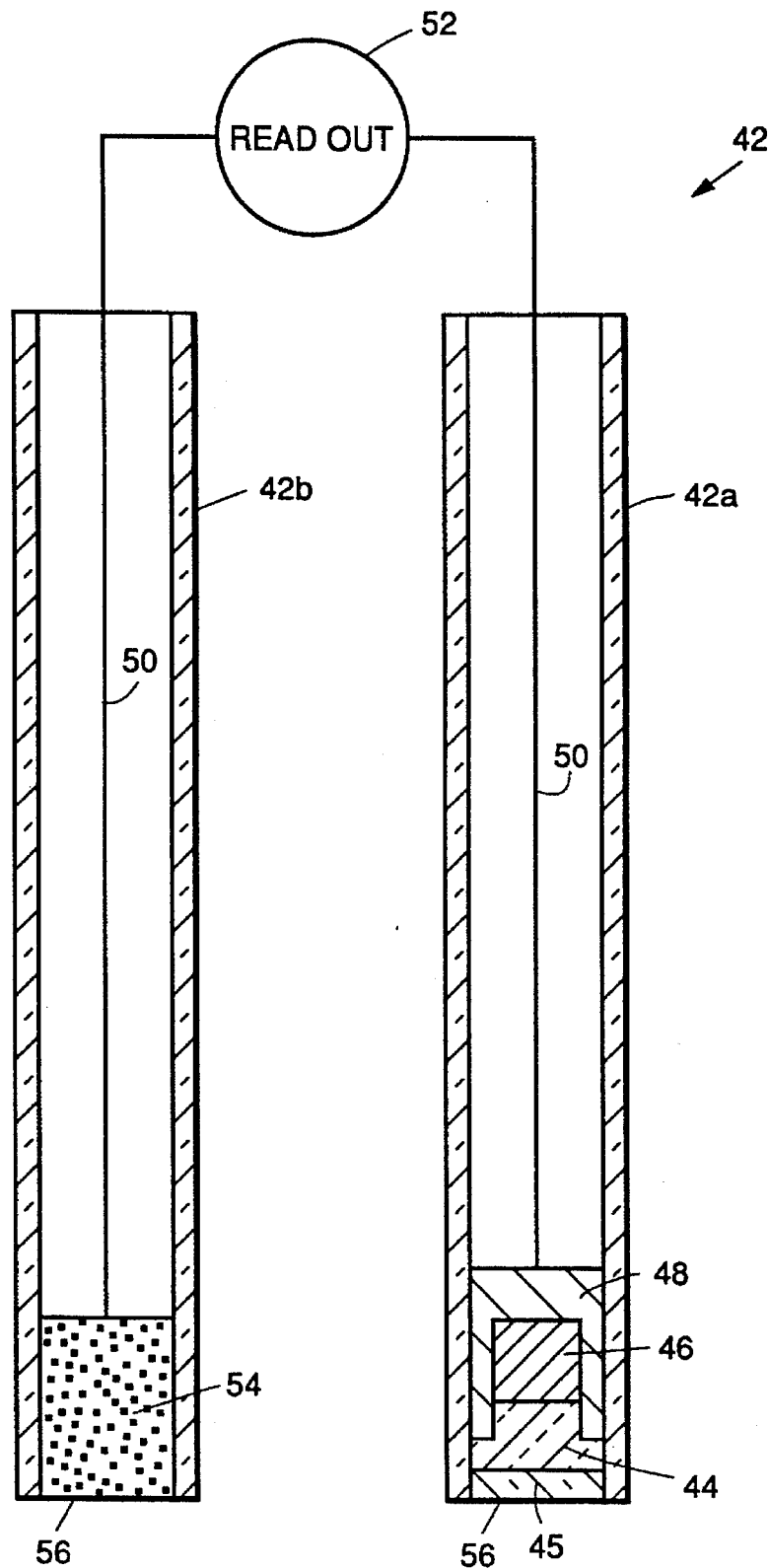
FIG. 3 is a cross-sectional view of the demag magnesium sensor of the present invention.

FIG. 3 illustrates the working elements of the sensor probe 42 of the present invention. The probe 42 comprises two electrodes 42a and 42b. One electrode 42a comprises a fibrous ceramic wick 44, a magnesium reference material 46, and a protective inverted molybdenum cup 48. The other electrode 42b comprises a graphite contact 54. Both electrodes are provided with molybdenum leads 50 shrouded in an inert gas. A voltage readout 52 connected to the molybdenum leads 50 provides a differential readout of the electromotive potential sensed between the two electrodes during use.

The selection of materials for use in the demag environment is very limited. While published data of thermodynamic and chemical properties can be used to narrow the range of candidates, final selections must be based on prolonged testing under service conditions. Many materials may resist attack by either molten magnesium or the molten chloride electrolyte, but few of them can withstand exposure to both substances. For example, graphite stands up well to the chloride melt but is slowly attacked by molten magnesium. Molybdenum resists the magnesium but is slowly attacked by the molten chlorides.

The ceramic wick 44 must comprise a material that is thermally and electrochemically stable with respect to molten magnesium. Furthermore, the wick must be an insulating material and must be wetted by the molten electrolyte. Alumina, normally considered a highly stable ceramic, reacts to form "spinel" ($MgAlO_4$) in this environment. Spinel itself, although difficult to fabricate, is the only ceramic that has demonstrated long-term resistance to the demag environment. Based on available data and the inventors' own limited testing, boron nitride (BN), yttrium oxide ($Y_2O_3$), and the oxides of the lanthanide elements, specifically, lanthanum, cerium, praseodymium, neodymium, samarium, europium, gadolinium, terbium, dysprosium, holmium, erbium, thulium, ytterbium, and lutetium, are other good candidates for the wick material.

However, practical considerations limit the ceramic wick 44 to yttrium oxide, inasmuch as this is the only ceramic material that reasonably meets the required criteria and is commercially available in fibrous form as felt material (Zircon Products, Florida, New York 10921). Use of materials that are not electrochemically stable would adversely affect the readout of the cell, and hence are to be avoided.

The yttrium oxide ceramic wick 44 is quite fragile. While it may be used alone, it is advantageously maintained in position by a porous ceramic plug 45, so that even if integrity of the fibrous mass 44 is compromised during repeated use, the yttrium oxide ceramic wick is still useable. The material comprising the porous ceramic plug 45 may comprise any of the ceramic materials listed above or zirconia.

The molybdenum leads 50 may be enshrouded in nitrogen or any of the inert gases, including helium, neon, argon, and the like, to prevent oxidation of the leads.

Figure 4A:
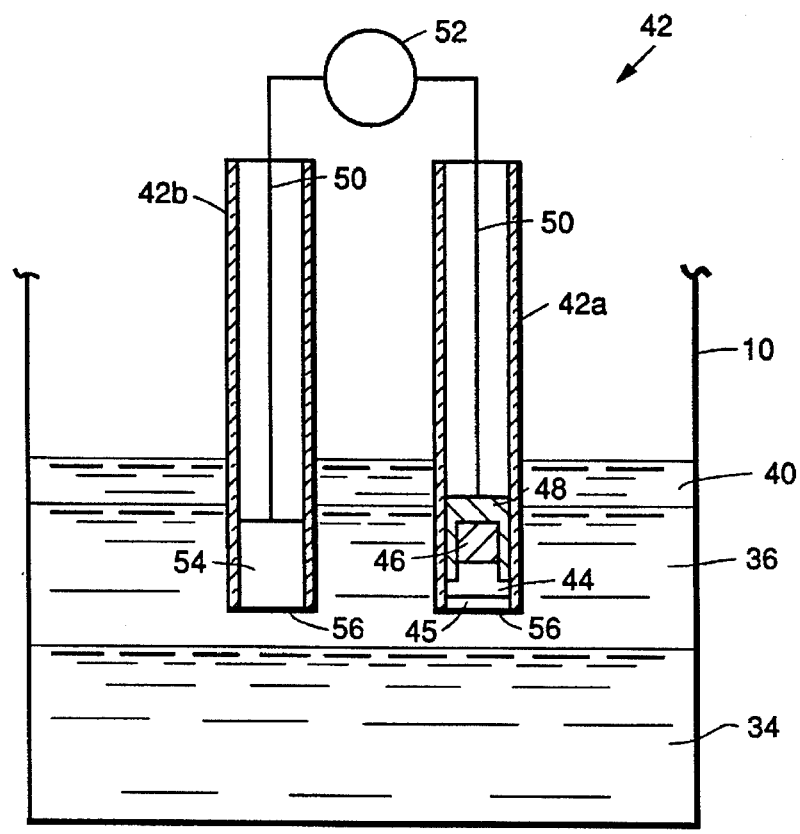
FIGS. 4a-b illustrate the sequential method of use of the magnesium sensor of the present invention, involving wetting a ceramic wick with molten salt (FIG. 4a) and then measuring the magnesium concentration in molten aluminum during demagging (FIG. 4b)
Figure 4B:
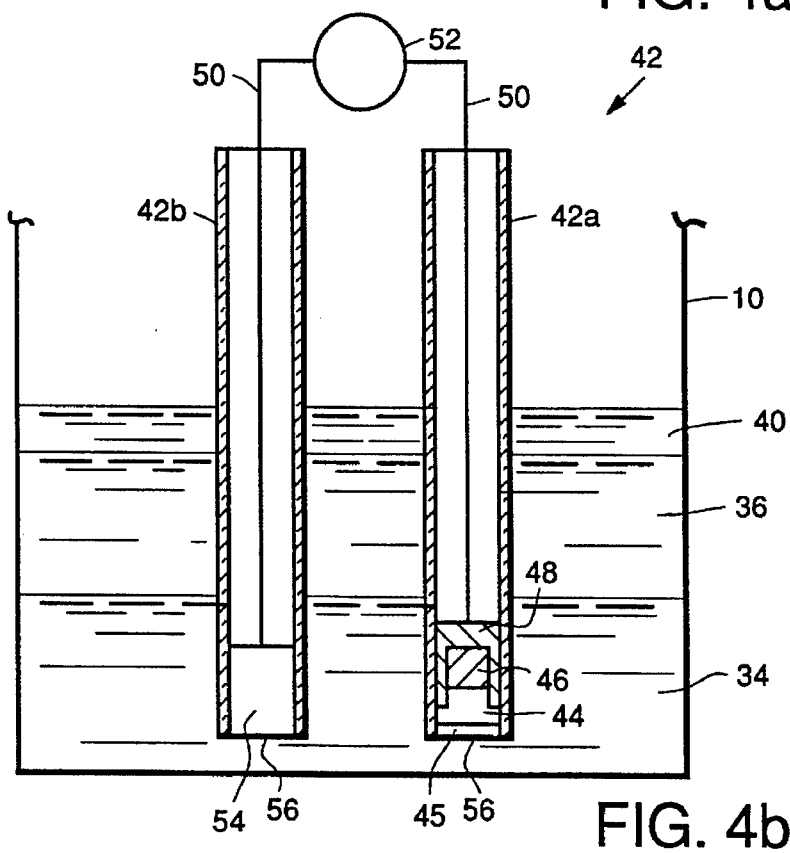

FIGS. 4a–b illustrates how the probe of the present invention is used in the demag operation. First, as shown in FIG. 4a, the tip 56 of the probe 42 is positioned in the molten salt layer 36 of the demag cell 10. This allows molten salt 36 to soak into the wick 44. Then, as shown in FIG. 4b, the probe is lowered until the tip 56 of the probe 42 is positioned within the bulk region of the processed aluminum 34. It is important that the measurement take place within the bulk region 34, since the top surface of the aluminum is being depleted of magnesium due to the demagging process. Because molten salt from layer 36 remains trapped in the wick 44, a small electrochemical cell is formed:

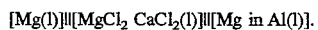

[Mg(l)]||[$MgCl_2$ $CaCl_2$(l)]||[Mg in Al(l)].

As indicated above, "l" refers to the indicated material as being in liquid (molten) form.

Once the molten salt 36 is in contact with the magnesium reference material 46, a differential potential is sensed between the two electrodes and is read out. Since the cell formed is a simple electrochemical concentration cell, the readout can be easily calibrated to magnesium concentration in molten aluminum. Once the readout indicates that the magnesium concentration in the molten aluminum has dropped below the desired maximum concentration, say, below 0.1%, then the purified molten aluminum 34 can be extracted from the demag cell 10 and the cell charged with fresh scrap aluminum for demagging.

For monitoring magnesium concentration in molten aluminum in real-time, the probe 42, once charged with molten salt 36, may be left in the aluminum region 34, typically on the order of hours, but may need to be moved into the molten salt region 36 periodically to recharge the probe.

Since Applicants' design involved a unique geometric construction (i.e., the wick 44), it was deemed necessary to perform certain tests to ensure that the demag process would not affect the operation of the probe 42 of the present invention. This was done through a series of room temperature experiments using low-cost materials. Some of the variables that were examined included the hydrostatic pressure, the ohmic drop due to the demagging current, and the concentration polarization in the aluminum.

Figure 5:
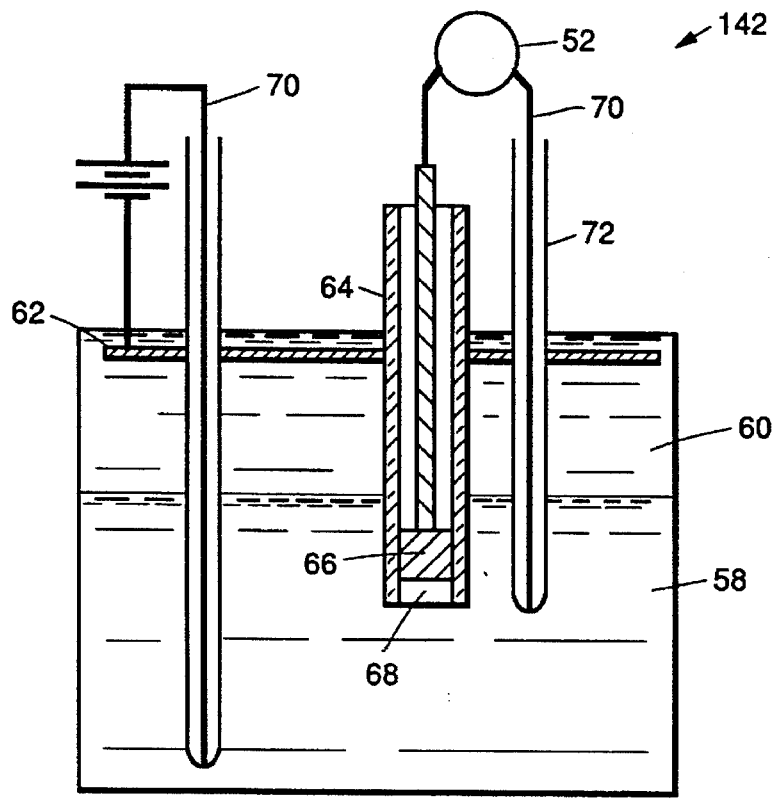
FIG. 5 illustrates a demag endpoint sensor employed in a room temperature simulation experiment to demonstrate feasibility of the present invention.

FIG. 5 illustrates the experimental setup used to perform these tests. Mercury with 1% indium (layer 58) was used to simulate the aluminum in the demag cell: mercury represented the aluminum, and indium represented the magnesium impurities. Floating on top of the mercury 58 was a solution of indium ions, specifically, a layer 60 of indium sulfamate. This was used to simulate the molten demag salt. Since the demag reaction vessel passes large quantities of electrical current through the molten material during the purification process, this was simulated as well. The power supply and stainless steel mesh assembly 62 on the left of FIG. 5 were used for this purpose. Finally, the magnesium sensor 42 was simulated using a probe 142 comprising a glass tube 64, a plug of indium 66, and a cotton wick 68. This is shown on the right of FIG. 5. Electrical contacts to the mercury pool 58 were made via platinum wires sealed in glass tubes.

Figure 6:
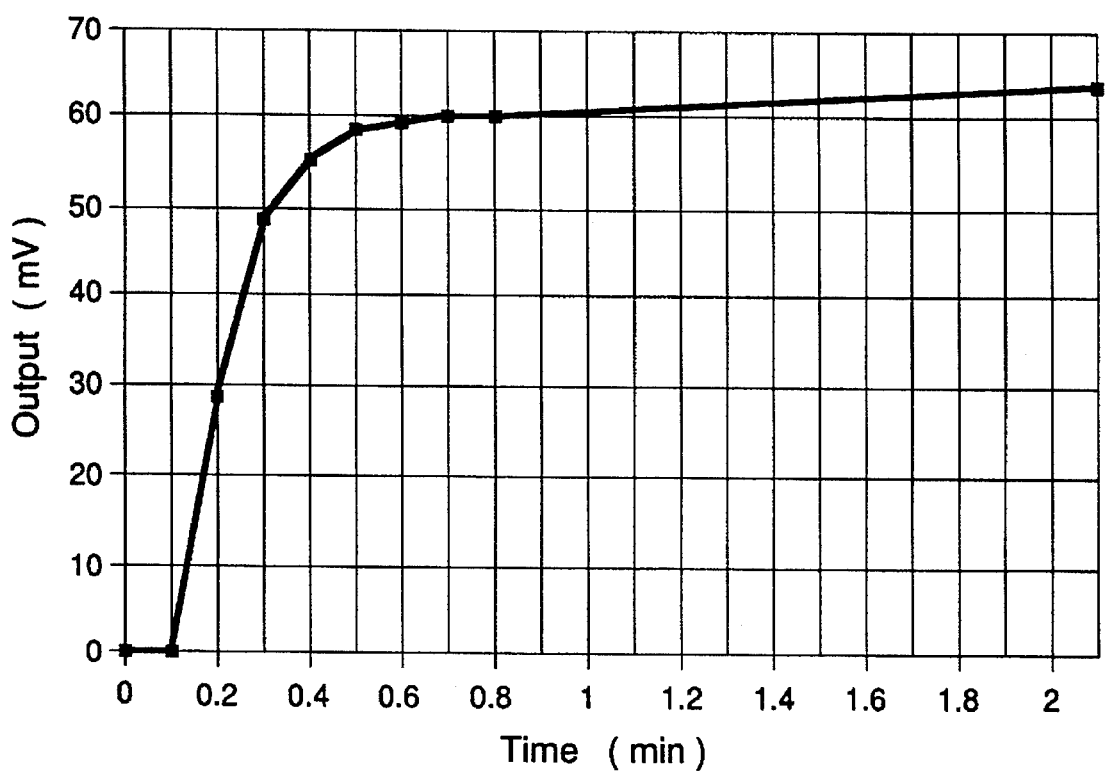
FIG. 6, on coordinates of sensor output (in millivolts) and time (in minutes), is a plot of the demag endpoint sensor room temperature simulation employed in the experiment of FIG. 5.

FIG. 6 illustrates the time required for the measurement to stabilize once the wick 68 is wetted. FIG. 7 illustrates the effect of hydrostatic pressure on the performance of the probe 142. FIG. 8 illustrates the change in the output of the probe 142 due to concentration polarization effects as a function of depth in the mercury 58.

High temperature experiments in a prototype zero-current demag cell were also performed, in which the cell was operated under conventional process conditions, but in the absence of any current. The zero-current demag cell contained the molten electrolyte 36 used in the commercial demag cell 10 and molten aluminum with 1% magnesium 34. The probe 42 performed as expected; the wick 44 wetted properly, the measurement was stable and within theoretical limits, and no signs of degradation of the wick material were observed.

The difference between the present invention and the one described in U.S. Pat. No. 4,601,810 is that the present invention uses a wick 44 to bring salt 36 from within the demag cell 10 into direct contact with the internal magnesium reference 46 of the probe, whereas U.S. Pat. No. 4,601,810 uses a built-in capsule of salt to contact the internal magnesium reference of their probe. The advantages of the probe 42 of the present invention due to this difference are as follows:

(A) In U.S. Pat. No. 4,601,810, the magnesium reference is held into proper position during the measurement by the buoyancy effect of the molten salt. When their probe is removed from the melt (i.e., the three molten liquid layers), the molten salt supporting the magnesium drains from the probe through the bottom frit. As a result, the molten magnesium drains from its protective molybdenum cup and defeats the purpose of their design.

In contrast, the present design uses a wick 44 to support the magnesium reference 46 in place. Since the wick 44 is a solid material and thus cannot drain, and since magnesium 46 cannot flow through the wick, the probe 42 of the present invention can be removed from the melt 34 and subsequently replaced without having the magnesium drain from its protective cup 48.

(B) Molten salts have a propensity to penetrate ceramic materials, particularly porous ceramics such as frits. When this occurs, the ceramic material loses mechanical strength. If, for example, the frit in the probe of U.S. Pat. No. 4,601,810 is damaged in this manner, it cannot be field-repaired.

Because the probe of the present invention uses a ceramic wick 44, i.e., fibrous ceramic packing, it can be field-repaired.

These advantages result in a probe 42 that is more robust and practical than the prior art design and that is amenable to foundry operating conditions.

Although the use of a wick in the probe of the present invention is novel, it should be pointed out that reducing this concept to practice was not trivial. Proper material selection of the wick was critical in achieving success in constructing the probe. In the probe of the present invention, the wick material is in direct contact with molten magnesium, molten aluminum, and molten chloride salts. Molten magnesium is very chemically reactive and has a propensity to chemically interact with most refractory materials, e.g., ceramics, which can significantly affect the measurement. Molten aluminum must not wet the wick or it will "short" the measurement. Molten magnesium must not wet the wick for the same reason. Molten chloride salts can penetrate refractory materials and weaken their mechanical strength. The molten salt must be able to wet the wick in order to form an electrical connection between the processed aluminum and the magnesium reference material contained in the probe. Additionally, the wick material must be commercially available.

Yttrium oxide is a material that meets all of these requirements. It is thermodynamically stable against magnesium, aluminum, and chloride salts. It is wetted by molten salts and is not wetted by either molten aluminum or molten magnesium. It is commercially available in either felt or textile form.

Thus, there has been disclosed a sensor probe for detecting the concentration of magnesium in molten aluminum and a method for using the same. It will be readily appreciated by those skilled in this art that various changes and modifications of an obvious nature may be made, and all such changes and modifications are considered to fall within the scope of the present invention as defined by the appended claims.

What is claimed is:

1. A sensor for real-time detecting and monitoring magnesium concentration in molten aluminum covered with a molten salt solution, said sensor probe comprising:

(a) first and second electrodes chemically inert with respect to molten magnesium and to molten aluminum, each electrode having two ends, with one end of each electrode provided with an electrical connection and the other end of each electrode adapted for immersion into said molten aluminum;

(b) readout means connected to each said electrical connection of each said electrode for detecting a change in electromotive potential between said other ends of each said electrode;

(c) said first electrode comprising an outer housing having a top and a bottom, a magnesium reference material, a support cup located within said outer housing and being open at one end for containing said magnesium reference material, and a first fibrous ceramic wick comprising yttrium oxide, wherein said first fibrous ceramic wick is positioned at said open end of said support cup in contact with said magnesium reference material to thereby retain said magnesium reference material in said support cup, said open end of said support cup comprising said other end of said first electrode and being adapted for receiving said molten salt solution therein whereby said molten salt solution becomes trapped in said first fibrous ceramic wick, said sensor probe adapted to provide an electrochemical cell comprising

[Mg(l)]‖[MgCl$_2$ CaCl$_2$(l)]‖[Mg in Al(l)], where "l" refers to liquid.

2. The sensor probe of claim 1 wherein said electrical connection to each of said electrodes comprises a molybdenum lead.

3. The sensor probe of claim 2 wherein said molybdenum leads are enshrouded in an inert gas selected from the group consisting of nitrogen, helium, neon, and argon.

4. The sensor probe of claim 1 wherein said support cup comprises molybdenum.

5. The sensor probe of claim 1 further including a second fibrous ceramic wick material located at said bottom of said outer housing, for maintaining said first fibrous ceramic wick in position.

6. The sensor probe of claim 5 wherein said second fibrous ceramic wick material is selected from the group consisting of zirconia, boron nitride, and oxides of the rare earth elements from lanthanum to lutetium, inclusive.

7. The sensor probe of claim 1 wherein said second electrode consists essentially of graphite.

8. A method of measuring magnesium concentration in molten aluminum during a process for reducing magnesium content in said molten aluminum, said process including forming a molten salt layer on said molten aluminum and passing a current through an anode immersed in said molten aluminum and a cathode immersed in said molten salt layer so as to ionize and collect said magnesium from said molten aluminum, said method comprising;

(a) providing a sensor probe comprising
  (1) first and second electrodes chemically inert with respect to molten magnesium and to molten aluminum, each electrode having two ends, with one end of each electrode provided with an electrical connection and the other end of each electrode adapted for immersion into said molten aluminum;
  (2) readout means connected to each said electrical connection of each said electrode for detecting a change in electromotive potential between said other ends of each said electrode;
  (3) said first electrode comprising an outer housing having a top and a bottom, a magnesium reference material, a support cup located within said outer housing and being open at one end for containing said magnesium reference material, and a first fibrous ceramic wick comprising yttrium oxide, wherein said first fibrous ceramic wick is positioned at said open end of said support cup in contact with said magnesium reference material to thereby retain said magnesium reference material in said support cup, said open end of said support cup comprising said other end of said first electrode and being adapted for receiving said molten salt therein, said sensor probe adapted to provide an electrochemical cell comprising

[Mg(l)]‖[MgCl$_2$ CaCl$_2$(l)]‖[Mg in Al (l)], where "l" refers to liquid;

(b) first immersing said sensor probe into said molten salt layer to wet said first fibrous ceramic wick with said molten salt wherein said molten salt remains trapped in said first wick;

(c) then immersing said sensor probe into said molten aluminum layer to contact said molten salt in said first fibrous ceramic wick with said molten aluminum; and (d) measuring change in potential as a function of time, said change in potential related to said magnesium concentration.

9. The method of claim 8 wherein said electrical connection to each of said electrodes comprises a molybdenum lead.

10. The method of claim 9 wherein said molybdenum leads are enshrouded in an inert gas selected from the group consisting of nitrogen, helium, neon, and argon.

11. The method of claim 8 wherein said support cup comprises molybdenum.

12. The method of claim 8 further including a second fibrous ceramic wick material located at said bottom of said outer housing, for maintaining said first fibrous ceramic wick in position.

13. The method of claim 12 wherein said second fibrous ceramic wick material is selected from the group consisting of zirconia, boron nitride, and oxides of the rare earth elements from lanthanum to lutetium, inclusive.

14. The method of claim 8 wherein said second electrode consists essentially of graphite.

15. The method of claim 8 wherein said probe is maintained in said molten aluminum layer for real-time monitoring of said magnesium concentration and is periodically moved into said molten salt layer to wet said first fibrous ceramic wick as needed.

* * * * *